(12) United States Patent
Height et al.

(10) Patent No.: US 6,929,235 B1
(45) Date of Patent: Aug. 16, 2005

(54) APPARATUS FOR FLOW RATE CONTROL

(75) Inventors: Murray J. Height, Somerville, MA (US); Eun Young Hwang, Cambridge, MA (US); Timothy J. Prestero, Jamaica Plain, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 58 days.

(21) Appl. No.: 10/408,396

(22) Filed: Apr. 7, 2003

Related U.S. Application Data

(60) Provisional application No. 60/373,849, filed on Apr. 19, 2002.

(51) Int. Cl.[7] .................................. F16K 7/04
(52) U.S. Cl. .......................... 251/4; 137/553
(58) Field of Search ............... 251/4, 7, 8; 137/553

(56) References Cited

U.S. PATENT DOCUMENTS

| | | |
|---|---|---|
| 1,959,074 A | 5/1934 | Bloxsom |
| 2,444,767 A | 7/1948 | Cobean |
| 2,595,511 A | 5/1952 | Butler |
| 3,299,904 A * | 1/1967 | Burke ........................... 251/9 |
| 3,332,439 A * | 7/1967 | Burke ........................... 251/8 |
| 3,570,531 A * | 3/1971 | McGay ........................... 251/7 |
| 3,800,794 A | 4/1974 | Georgi |
| 3,915,167 A | 10/1975 | Waterman |
| 3,984,081 A | 10/1976 | Hoganson |
| 4,037,598 A | 7/1977 | Georgi |
| 4,061,700 A | 12/1977 | Gallivan |
| 4,238,108 A | 12/1980 | Muetterties |
| 4,261,388 A | 4/1981 | Shelton |
| 4,270,725 A | 6/1981 | Scott et al. |
| 4,312,493 A * | 1/1982 | Stauffer ......................... 251/8 |
| 4,337,791 A * | 7/1982 | Tech et al. ..................... 251/8 |
| 4,338,932 A | 7/1982 | Georgi et al. |
| 4,403,764 A | 9/1983 | Repplinger |
| 4,452,273 A | 6/1984 | Hanzawa et al. |
| 4,457,750 A | 7/1984 | Hill |
| D280,763 S | 9/1985 | Kulle |
| 4,576,593 A * | 3/1986 | Mommer ....................... 251/4 |
| 4,585,442 A | 4/1986 | Mannes |
| 4,601,700 A | 7/1986 | Thompson et al. |
| 4,662,599 A | 5/1987 | Attermeier |
| 4,769,004 A * | 9/1988 | Poindexter ..................... 251/4 |
| 4,802,506 A | 2/1989 | Aslanian |
| 4,807,660 A | 2/1989 | Aslanian |
| 4,869,721 A | 9/1989 | Karpisek |

(Continued)

*Primary Examiner*—John Bastianelli
(74) *Attorney, Agent, or Firm*—Daly, Crowley, Mofford & Durkee, LLP

(57) ABSTRACT

A clamp having a first clamp body, a second clamp body, and a clamping structure coupled to at least one of the first and second clamp bodies. One or both of the clamp bodies form a channel adapted to receive a tube. The clamping structure is movable in the channel to control the flow rate of a fluid flowing through the tube. In one embodiment, the clamp is provided as a rotary clamp having clamp bodies that are adapted to be rotated relative to each other to control the flow rate of a fluid through a tube disposed in the rotary clamp. The rotary clamp has a substantially linear, or otherwise pre-determined, relationship between flow rate of a fluid flowing through the tube and rotation of the second clamp body.

8 Claims, 6 Drawing Sheets

U.S. PATENT DOCUMENTS

| | | |
|---|---|---|
| 4,919,389 A | 4/1990 | Hoekwater et al. |
| 4,974,811 A | 12/1990 | Ishida |
| 5,000,419 A * | 3/1991 | Palmer et al. .................. 251/9 |
| 5,045,069 A * | 9/1991 | Imparato .................... 604/253 |
| 5,097,859 A * | 3/1992 | Grabenkort et al. ........... 251/7 |
| 5,190,079 A | 3/1993 | Nakada |
| 5,197,708 A * | 3/1993 | Campau ........................ 251/8 |
| 5,259,587 A | 11/1993 | DAlessio et al. |
| 5,718,409 A | 2/1998 | Starchevich |
| 5,728,077 A | 3/1998 | Williams et al. |
| 5,980,490 A | 11/1999 | Tsoukalis |
| 6,129,330 A | 10/2000 | Guala |
| 6,343,619 B1 | 2/2002 | Pruitt |

* cited by examiner

APPARATUS FOR FLOW RATE CONTROL

CROSS REFERENCE TO RELATED APPLICATIONS

The present application claims the benefit under 35 U.S.C. §119(e) of U.S. Provisional Patent Application No. 60/373,849, filed on Apr. 19, 2002, which is incorporated herein by reference in its entirety.

STATEMENT REGARDING FEDERALLY SPONSORED RESEARCH

Not Applicable.

FIELD OF THE INVENTION

This invention relates generally to flow rate control devices and more particularly to devices that control the flow rate of a fluid flowing through a tube.

BACKGROUND OF THE INVENTION

As is known in the art, there are certain medical conditions which, if not treated, can lead to severe dehydration and death. Cholera is one example of such a medical condition. To treat cholera and other conditions, an intravenous (IV) drip infusion is often used to re-hydrate patients and/or to introduce medicine into a patient's body. An intravenous drip infusion of saline is the preferred technique for the medical treatment of severe cholera. In a cholera epidemic, where many patients need to be treated as quickly as possible, it is desirable set up IV equipment and initiate treatment as rapidly as possible.

As is also known in the art, a conventional IV drip set includes a fluid reservoir, a clear plastic drip chamber coupled to the fluid reservoir for visualization of fluid flow, a clear flexible tube coupled to the drip chamber, a roller clamp coupled to the flexible tube for flow rate control, and an attachment to connect the flexible tube to an intravenous catheter adapted to be placed into a patient. The roller clamp provides an adjustable force upon the flexible tube and therefore an adjustable flow restriction. The rate at which fluid flows through the tube is estimated by observing the drip rate in the drip chamber. The rate at which the fluid flows through the tube is adjusted by adjusting the roller clamp until the desired drip rate is achieved. Such conventional IV drip sets are simple, relatively inexpensive and find widespread use. One example of a conventional IV drip set is further described in conjunction with FIG. 1 below.

When using the IV drip set, it is important for the user to accurately regulate the flow of fluid (e.g. saline solution) into the patient. The roller clamp is used to adjust the flow rate of the fluid flowing through the flexible tube and therefore the flow rate into the catheter, which is inserted into the patient's body. A user turns an adjustment roller on the roller clamp to provide more or less force, or clamping action, upon the flexible tube and therefore more or less restriction of the flexible tube, thereby adjustably controlling the flow rate.

It is relatively difficult for a user to accurately adjust conventional roller clamps to accurately provide a specific flow rate. Thus, to arrive at a specific flow rate, it is often necessary to make an adjustment, observe the resultant flow rate via the drip chamber, and then re-adjust as necessary. These steps are repeated until arriving at a desired specific flow rate. Flow rate adjustment can, therefore, be a relatively time-consuming task.

The difficulty in adjusting the flow rate is due in part to a large non-linearity in flow rate control provided by conventional roller clamps. Essentially, as the user turns the adjustment roller of the conventional roller clamp, the flow rate is not linearly adjusted in proportion to the rotation of the adjustment roller. The non-linearity is sufficiently great that even a slight rotation of the adjustment roller in either direction can cause an undesired flow rate either higher or lower than the desired flow rate. Furthermore, with each adjustment of the adjustment roller, the drip rate in the drip chamber must be observed to determine the flow rate. Observation of the drip rate involves counting a number of drips over a time period, for example, 15 seconds. As described above, particularly in epidemic situations, it is necessary that set up of the IV drip set, including adjustment of the flow rate, be done quickly. Difficulty of flow rate adjustment slows the set up process.

Therefore, it would be desirable to provide a flow control apparatus that can be quickly adjusted to achieve a desired flow rate of a fluid flowing through a tube and into a catheter. It would be further desirable to provide a flow rate apparatus, which is relatively low cost and simple. It would also be desirable to provide a flow control apparatus that is manual and that requires no power supply.

SUMMARY OF THE INVENTION

In accordance with the present invention, an apparatus for flow rate control of fluid includes a first clamp body having a channel with a depth which varies as a predetermined function of position along the channel. The first clamp body is coupled to a second clamp body that has a clamping feature disposed into the channel. When a tube is placed in the channel, the second clamp body can be rotated relative to the first clamp body to provide a selected force upon the tube and therefore a selectable restriction in the tube. The selectable restriction provides a selectable flow rate of the fluid flowing through the tube. In one particular embodiment, the predetermined function provides a control of fluid flowing through the tube that is substantially linearly proportional to rotation of the second clamp body. In one particular embodiment, a scale can be associated with the second clamp body and the first clamp body to indicate the flow rate.

With this particular arrangement, the apparatus for flow rate control provides the user with the ability to rapidly set up and control the flow rate of the fluid. Having a visual scale allows the user to rapidly set the apparatus to a known flow rate.

BRIEF DESCRIPTION OF THE DRAWINGS

The foregoing features of the invention, as well as the invention itself may be more fully understood from the following detailed description of the drawings, in which.

DETAILED DESCRIPTION OF THE INVENTION

Figure 1:
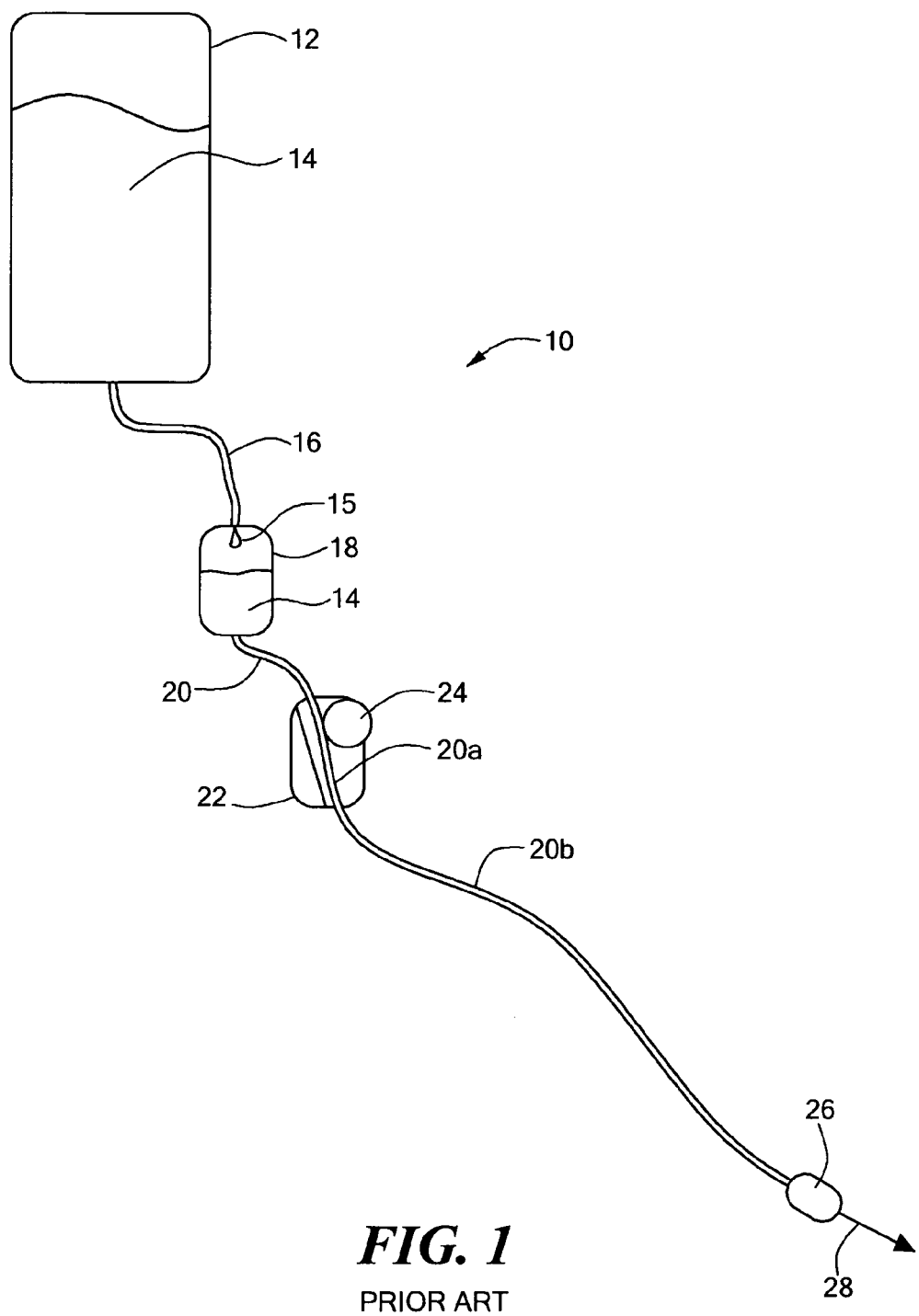
FIG. 1 is a view of a prior art intravenous (IV) drip set.

Referring now to FIG. 1, a prior art intravenous (IV) drip set 10 includes a fluid reservoir 12 containing a fluid 14. The fluid reservoir 12 can be provided, for example, as a conventional fluid bag (e.g., saline or blood) or as any type of other fluid container. The IV drip set 10 also includes a drip chamber 18 coupled to the fluid reservoir 12 with a tube 16. The drip chamber 18 allows a user to view the flow rate of the fluid 14a flowing in the tube 16 by viewing a drip rate of falling drops 15. The fluid 14 flows out of the drip chamber 18 and into a tube 20 having tube portions 20a and 20b. The tube 20 can be one of a variety of compressible tubes. For example, in one particular embodiment, the tube 20 is a flexible plastic tube. A roller clamp 22 having an adjustment roller 24 is coupled to the tube portion 20a. The tube portion 20b is coupled with an attachment 26 to a catheter 28, which is inserted into a patient (or an animal).

The prior art roller clamp 22 is described in detail in conjunction with FIG. 2 below. Suffice it here to say that, in operation, the roller clamp 22 provides a variable force, and therefore, a variable compression, upon the tube portion 20a, in proportion to manual rotation of the adjustment roller 24 by a user. The variable compression provides a selectable restriction of the tube portion 20b. Therefore, by observing the rate of drops 15 falling in the drip chamber 18, and turning the adjustment roller 24 in order to select a drip rate, a user selects a flow rate of the fluid 14 flowing through the tube 20 and into the arm of the patient.

Figure 2:
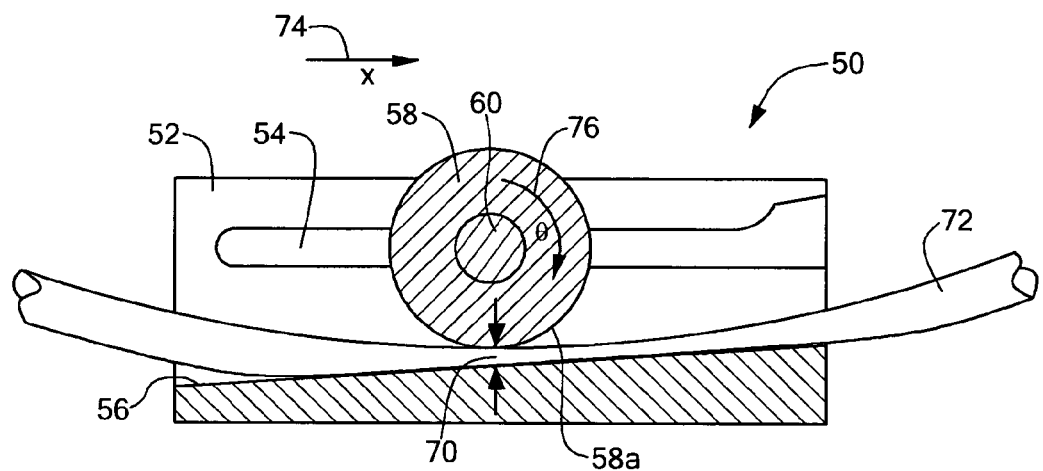
FIG. 2 is a cross-sectional view of an exemplary prior art roller clamp coupled to a tube.

Referring now to FIG. 2, an exemplary prior art roller clamp 50, shown in a cross-sectional view, includes a clamp body 52, having an adjustment roller track 54 and a clamp body surface 56. An adjustment roller 58 is coupled to the clamp body 52 by way of an axle 60 that can move along the adjustment roller track 54. The adjustment roller track 54 of the prior art roller clamp 50 is substantially linear. The clamp body surface 56 of the prior art roller clamp 50 is also substantially linear, i.e., the adjustment roller track 54 has a planar surface in an x-direction 74 in which the adjustment roller 58 can move along the adjustment roller track 54. The clamp body surface 56 is at a substantially constant angle relative to the adjustment roller track 54.

The roller clamp 50 is adapted to couple to a tube 72, such that the tube 72 is disposed between a surface 58a of the adjustment roller 58 and the clamp body surface 56. The tube 72 can correspond, for example, to the tube portion 20a of FIG. 1. When the user turns the adjustment roller 58, the adjustment roller 58, having friction against the tube 72, moves along the tube 72, thereby moving along the adjustment roller track 54. As the adjustment roller 58 is turned, moving along the adjustment roller track 54, the clamp body 52 remains substantially stationary relative to the tube 72.

A variable gap 70 between the adjustment roller surface 58a and the clamp body surface 56 has a size proportional to the location of the adjustment roller 58 along the adjustment roller track 54. Turning the adjustment roller 58 in a clockwise-direction 76 tends to move the adjustment roller 58 in the x-direction 74. Since the clamp body surface 56 is at an angle with respect to the adjustment roller track 54, the width of the variable gap 70 decreases as the adjustment roller 58 turns in a clockwise direction (i.e., toward the right of FIG. 2). Conversely, the width of the variable gap 70 increases as the adjustment roller 58 turns in a counter clockwise direction (i.e., toward the left in FIG. 2). Reducing the size of the variable gap 70 causes the tube 72, disposed into the variable gap 70, to compress by a greater amount, thereby decreasing flow rate of a fluid flowing through the tube 72.

The conventional roller clamp 50 provides a very non-linear relationship between the position (i.e., the rotation) of the adjustment roller 58 and the flow rate. At some flow rate settings, even a slight rotation of the adjustment roller in either direction can cause the flow rate to be outside of desired bounds.

Figure 3:
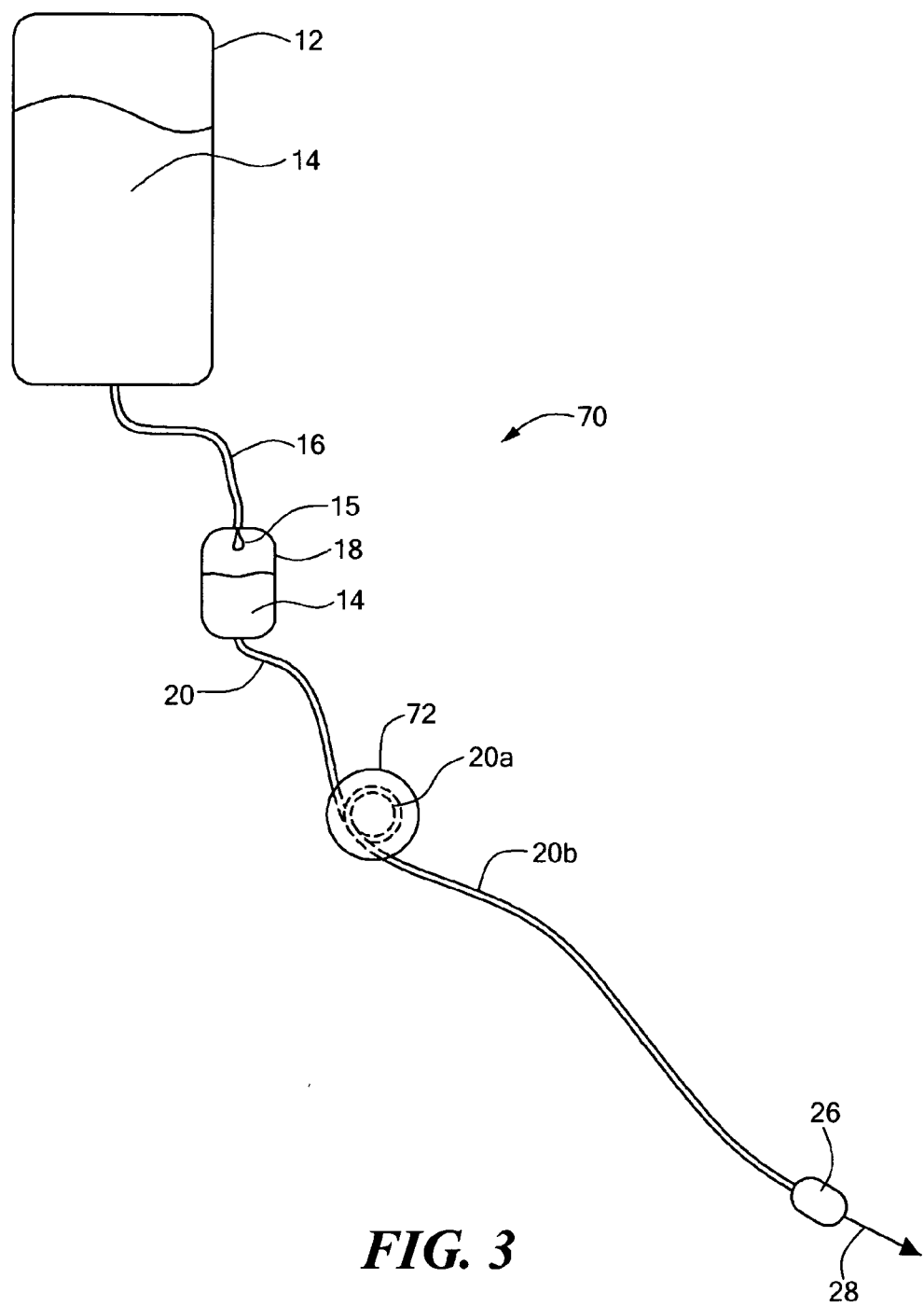
FIG. 3 is a view of an exemplary rotary clamp in accordance with the present invention coupled to a tube as used in an IV drip set.

Referring now to FIG. 3, an exemplary IV drip set 70, in which like elements of FIG. 1 are shown having like reference designations, includes a rotary clamp 72 in accordance with the present invention in place of the conventional roller clamp 22 (FIG. 1). The rotary clamp 72 is coupled to the tube portion 20a and provides an adjustable flow rate of the fluid 14 flowing though the tube 20. The rotary clamp 72 is described in greater detail below.

Figure 4:
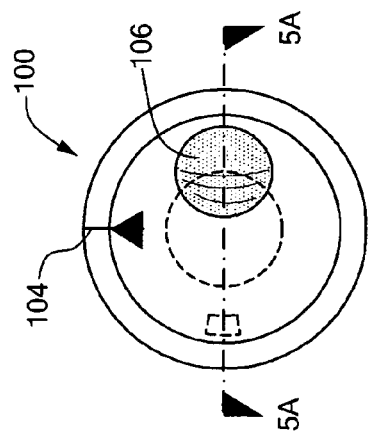
FIG. 4 is a top view of an exemplary first clamp body used in the rotary clamp of FIG. 3.

Referring now to FIG. 4, an exemplary first clamp body 80 used as part of a rotary clamp, for example the exemplary rotary clamp 72 of FIG. 3, includes a channel 86 adapted to be coupled to a tube 84. The tube 84 can be the same as or similar to the tube portion 20a of FIG. 3. The channel 86 can be a circumferential channel, therefore, the tube 84 placed therein forms a loop. The first clamp body 80 also includes a central hole 88, here shown as a through-hole 88 passing all the way through the first clamp body 84. The channel 86 can be a circumferential channel, therefore, the tube 84 placed therein forms a loop. The first clamp body 82 also includes a central hole 88, here shown as a through-hole 88 passing all the way through the first clamp body 84.

Figure 4A:
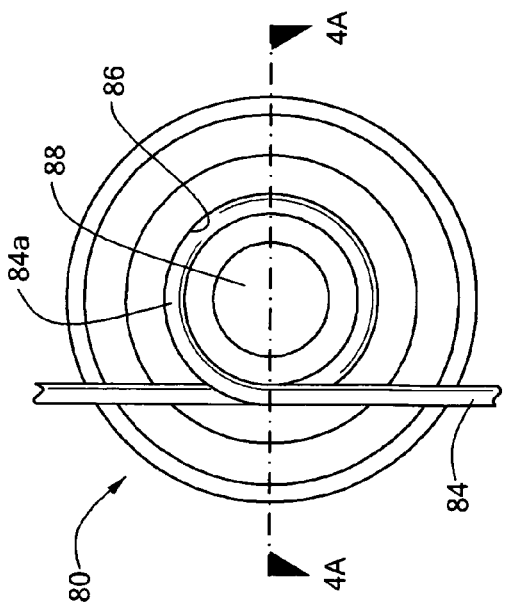
FIG. 4A is a cross sectional view of the exemplary first clamp body of FIG. 4 taken along line 4A—4A of FIG. 4.

Referring now to FIG. 4A, in which like elements of FIG. 4 are shown having like reference designations, the exemplary first clamp body 80 includes the channel 86, into which the tube 84 is disposed. The exemplary first clamp body has a first surface 80a and a second surface 80b.

Figure 5:
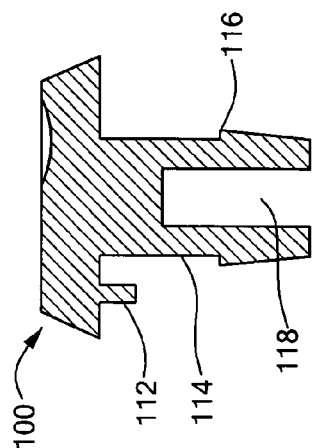
FIG. 5 is a top view of an exemplary second clamp body used in the rotary clamp of FIG. 3.

Referring now to FIG. 5, an exemplary second clamp body 100 used as part of a rotary clamp, for example the exemplary rotary clamp 72 of FIG. 3, includes an indicator 104, which can be used as a reference to show a rotational position of the second clamp body 100. The second clamp body 100 can also include a depression 106, which helps a user to grip the second clamp body 100 with a thumb or finger.

Figure 5A:
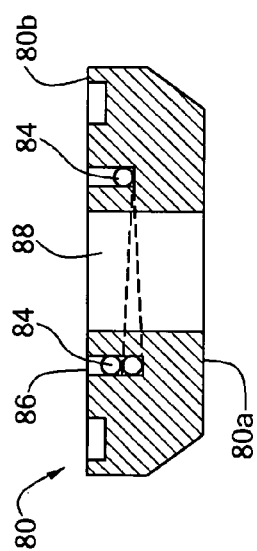
FIG. 5A is a cross sectional view of the exemplary second clamp body of FIG. 5 taken along the line 5A—5A of FIG. 5.

Referring now to FIG. 5A, in which like elements of FIG. 5 are shown having like reference designations, the exemplary second clamp body 100 includes a clamping structure 112 and a cylindrical center portion 114. The cylindrical center portion 114 can have a relief slot 118 and a retention surface 116 which is here provided as a detent.

When assembled, the cylindrical center portion 114 of the second clamp body 100 is disposed in the central hole 88 (FIGS. 4–4A) of the first clamp body 80 (FIGS. 4–4A). The retention surface 116 engages an engagement region on body 80. In this example, the retention surface 116 engages a portion of surface 80a the first of clamp body 80. It should be appreciated that when the cylindrical center portion 114 is disposed in opening 88, the clamp bodies 80, 100 are moveable (i.e., rotatable) with respect to each other. The second clamp body 100 is thus coupled to the first clamp body 80 by the retention surface 116. Also, with the second clamp body 100 disposed in opening 88, the clamping structure 112 is aligned with the channel 86, and is generally in contact with the tube 84 (FIGS. 4–4A), providing a compression thereupon.

It should be appreciated that, although in this example the first clamp body 80 is coupled to the second clamp body 100 by a detent or mechanical catch structure (e.g. structure 116 and surface 80*a*), any mechanism for coupling the clamp bodies 80, 100 may be used as long as the mechanism allows the clamping structure 112 to move along channel 86. In an alternate embodiment, the clamp bodies 80, 100 could be provided having a series of individual clamping structures disposed in different regions of the channel 86. By pushing down on different ones of such clamping structures, a flow rate can be changed.

Figure 6:
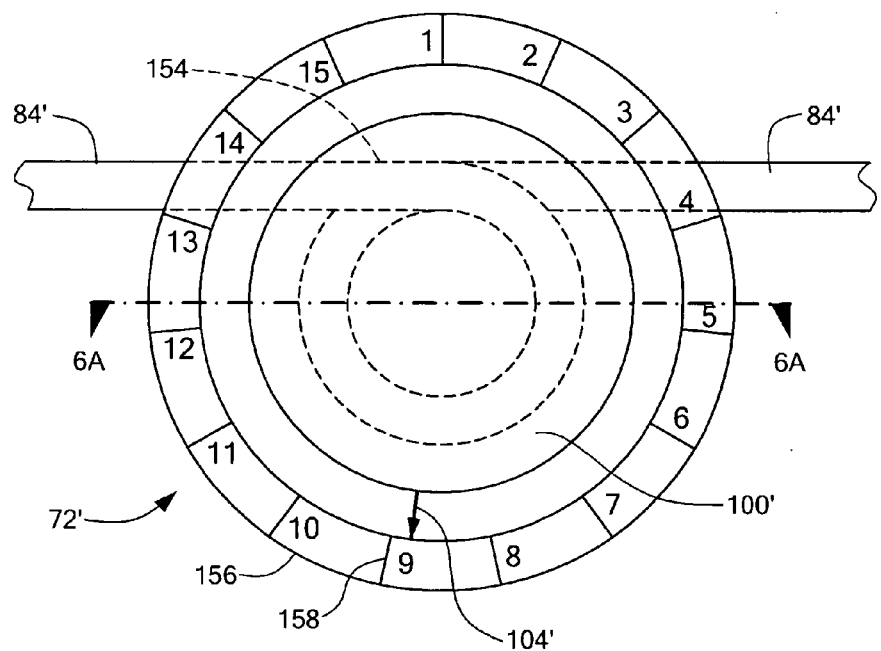
FIG. 6 is a top view of an exemplary rotary clamp in accordance with the present invention.

Referring now to FIG. 6, an exemplary rotary clamp 72', shown in a top view, can be the same as or similar to the exemplary rotary clamp 72 of FIG. 3. The rotary clamp 72' is adapted to be coupled to a tube 84', which forms a coil 154 in a channel (not shown) within the rotary clamp 72'. The exemplary rotary clamp 72' includes a second clamp body 100' having an indicator 104'. A ring scale 156 can be disposed about an edge of the rotary clamp 72'. The ring scale 156 can have one or more graduations, of which graduation 158 is but one example. In operation, the indicator 104' can be used in conjunction with the ring scale 156 to indicate rotational position of the second clamp body 100' relative to a first clamp body (not visible in FIG. 6).

Figure 6A:
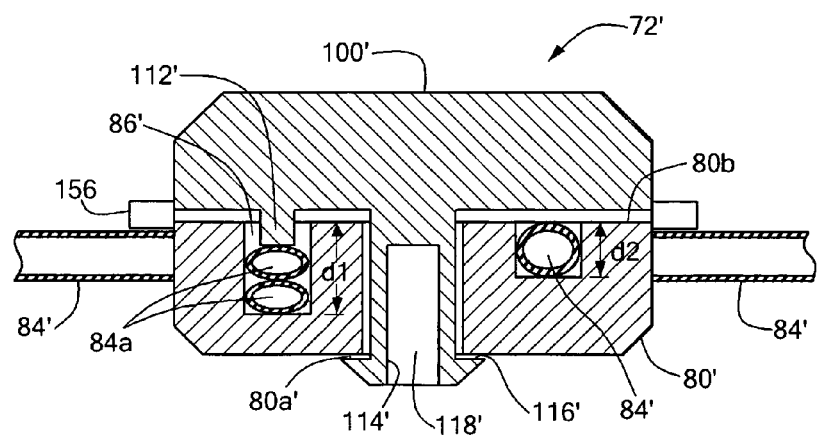
FIG. 6A is a cross sectional view of the exemplary rotary clamp of FIG. 7 taken along the line 6A—6A of FIG. 6.

Referring now to FIG. 6A, in which like elements of FIG. 6 are shown having like reference designations, the exemplary rotary clamp 72' of FIG. 6, shown in a cross-sectional view taken along line 6A—6A of FIG. 6, includes the second clamp body 100' having a clamping structure 112'. The clamping structure 112' can be similar to or the same as the clamping structure 112 of FIG. 5A. The second clamp body 100' also has a cylindrical center portion 114' having a relief slot 118' and a retention surface 116'. The cylindrical center portion 114' can be the same as or similar to the cylindrical center portion 114 of FIG. 5A, which also has the similar relief slot 118 and the similar retention surface 116.

The exemplary rotary clamp 72' also includes a first clamp body 80' having a channel 86'. The first clamp body 80' can be the same as or similar to the first clamp body 80 of FIGS. 4–4A. The channel can be a circumferential channel 86', which can be the same as or similar to the circumferential channel 86 of FIG. 4A. The circumferential channel 86' has a variable depth d1, d2, which is a function of position along the channel 86'. As shown, the depth d1 at a first position along the channel 86' has the depth d1 that is deeper (as measured from surface 80*b*) than the depth d2 at a second position the channel 86'.

The second clamp body 100' is coupled to the first clamp body 80' by way of contact between the retention surface 116' and a surface 80*a'* of the first clamp body 80'. In operation, the clamping structure 112' compresses the tube 84' in proportion to depth of the channel 86' at a position along the channel 86' corresponding to the location of the clamping structure 112'. In the orientation shown, for example, the clamping structure 112' compresses the tube portion 84*a'* in proportion to the depth d1. Compression of a tube, for example, the tube portion 84*a'*, effects flow rate of a fluid, which can be a liquid, a gas, or a mixed phase combination of any of a liquid, a gas, and solids, flowing through the tube 84'.

The channel 86' has a depth (here shown as depths d1, d2) that varies as a pre-determined function of position along the channel 86'. Therefore, when a user rotates the second clamp body 100' relative to the first clamp body 80', the clamping structure 112' compresses the tube 84' (e.g. tube portion 84*a'*) by an amount which depends upon the location of the clamp structure 112' within the channel 86'. That is, the amount by which the tube 84' is compressed varies in proportion to the rotation of clamp body 100' relative to the clamp body 80'. With this particular arrangement, the flow rate of fluid flowing through the tube 84' varies in proportion to rotation of the second clamp body 100' relative to the first clamp body 80'.

The channel 86', having the depth that varies as a pre-determined function of position along the channel 86', can provide a flow rate control of fluid flowing through the tube 84', which is substantially linearly proportional to relative rotation of the second clamp body 100' to the first clamp body 80'. However, in other embodiments, the channel 86' can have a depth that varies as a different pre-determined function of position along the channel 86', and therefore, can provide a non-linear pre-determined function of flow rate versus rotation of the second clamp body 100'. It should be appreciated that the channel 86' can be provided having a smooth surface or a stepped surface.

The ring scale 156 can be permanently affixed to the rotary clamp 72', for example as a ring scale 156 molded into the first clamp body 80'. In an alternate embodiment, the scale can be affixed to the rotary clamp 72' with tape, adhesive, or the like.

Figure 6B:
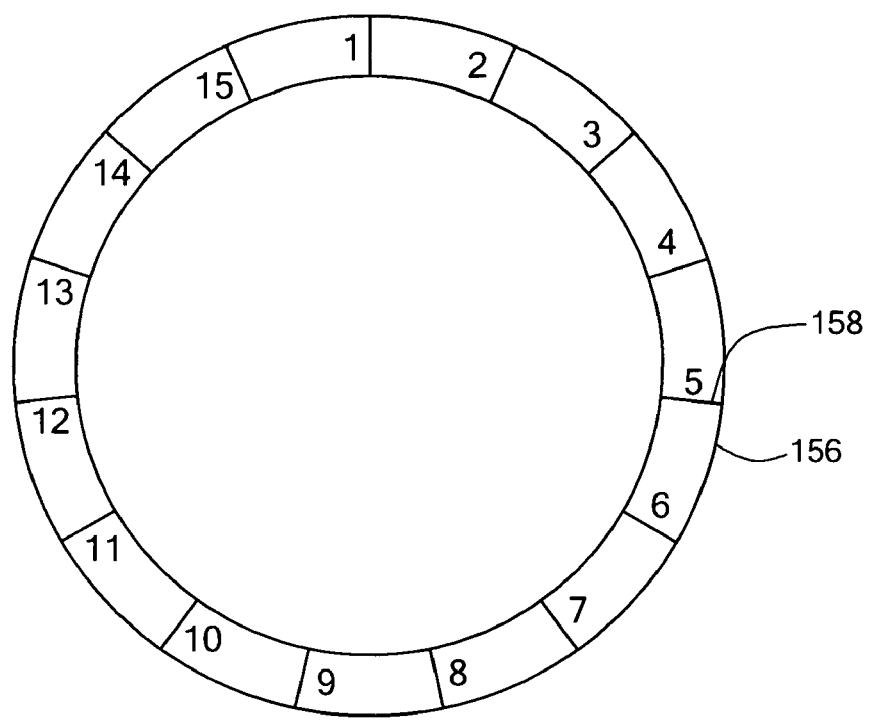
FIG. 6B is a top view of a ring scale that can be used in conjunction with the first clamp body of FIGS. 4–4A and the second clamp body of FIGS. 5–5A.

Referring briefly now to FIG. 6B, the ring scale 156 can be provided in conjunction with the first clamp body 80 (FIGS. 4–4A) and the second clamp body 100 (FIGS. 5–5A). The ring scale can include one or more graduations, of which graduation 158 is but one example. When assembled, as shown in FIGS. 6 and 6A, the ring scale 156 can provide an indication of the degrees of rotation of the second clamp body 100' relative to the first clamp body 80'. The ring scale 156, in combination with the indicator 104' (FIG. 6), can indicate the amount of rotation of the second clamp body 100' relative to the first clamp body 80'. As explained below, the relative positions of the first and second clamp bodies 80' and 100' corresponds to flow rate of the fluid flowing though the tube 84'.

Referring again to FIG. 6A, the ring scale 156, in combination with the indicator 104' (FIG. 6), provides a visual indication of position of the second clamp body 100', and therefore, a visual indication of the flow rate through the tube 84' to which the rotary clamp 72' is coupled. The user can therefore rapidly and accurately rotate the second clamp body 100' to a desired position relative to the ring scale 156 to set a desired flow rate. The ring scale can have graduations 158 with or without associated numerical labels. The numerical labels can represent flow rate in desired units, for example in mL/min or in drops per minute, equivalent to the drip chamber (e.g., 18, FIG. 1), or in any other units corresponding to flow rate.

While the ring scale 156 has been described, it should be appreciated that scales having other configurations can be applied to this invention to indicate the rotation of the second clamp body 100' relative to the first clamp body 80'. For example, in one particular embodiment, a screw scale can be disposed on a screw structure that moves along an axis of rotation of the second clamp body 100' in response to rotation of the second clamp body 100'.

Also, while the channel 86' has been herein shown and described to be a circumferential channel 86', in other embodiments, a channel having another shape can also be used. For example, a channel can be provided having an oval shape, rectangular shape (i.e. four sides), octagonal shape (i.e. eight sides) or any shape (including irregular shapes) having any number of sides.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. An apparatus to control the flow rate of a fluid, comprising:
    a first clamp body having a channel with a shape curved in a direction along a length of the channel and with a depth that varies as a predetermined function of angular position along the length of the channel;
    a second clamp body coupled to said first clamp body; and
    a clamping structure coupled to at least one of said first and second clamp bodies, movably disposed in the channel.

2. The apparatus of claim 1, wherein said first clamp body is adapted to receive a tube and said clamping structure is adapted to contact the tube.

3. The apparatus of claim 2, wherein the channel has a selected one of a substantially annular shape and a spiral shape, and wherein said second clamp body can be rotated relative to said first clamp body such that said clamping structure provides a selected force upon the tube disposed in the channel.

4. The apparatus of claim 3, wherein the flow rate of the fluid is substantially linearly proportional to the rotation of said second clamp body relative to said first clamp body.

5. The apparatus of claim 1, further including a calibrated scale associated with at least one of said first clamp body and said second clamp body, wherein said calibrated scale indicates a flow rate value corresponding to the flow rate of the fluid.

6. The apparatus of claim 5, wherein said calibrated scale has a linear scale with respect to rotation angle.

7. The apparatus of claim 5, wherein said calibrated scale has a non-linear scale with respect to rotation angle.

8. The apparatus of claim 1, wherein the channel is provided having a series of steps, with at least a first one of the steps giving a channel depth which is different than the channel depth of a second one of the steps.

* * * * *

UNITED STATES PATENT AND TRADEMARK OFFICE
CERTIFICATE OF CORRECTION

| | | |
|---|---|---|
| PATENT NO. | : 6,929,235 B1 | Page 1 of 1 |
| APPLICATION NO. | : 10/408396 | |
| DATED | : August 16, 2005 | |
| INVENTOR(S) | : Height et al. | |

It is certified that error appears in the above-identified patent and that said Letters Patent is hereby corrected as shown below:

Column 1, line 32 delete " desirable set up" and replace it with --desirable to set up--.

Column 4, line 36-40 delete "The channel 86 can be a circumferential channel, therefore, the tube 84 placed therein forms a loop. The first clamp body 82 also includes a central hole 88, here shown as a through-hole 88 passing all the way through the first clamp body 84."

Signed and Sealed this

First Day of August, 2006

JON W. DUDAS
*Director of the United States Patent and Trademark Office*